United States Patent [19]

Evans et al.

[11] Patent Number: 4,734,369

[45] Date of Patent: Mar. 29, 1988

[54] TISSUE CULTURES OF LYCOPERSICON SPP.

[75] Inventors: David A. Evans, Palmyra; William R. Sharp, Haddenfield, both of N.J.

[73] Assignee: Campbell Soup Company, Camden, N.J.

[21] Appl. No.: 525,106

[22] Filed: Aug. 22, 1983

[51] Int. Cl.$^4$ .................... C12N 5/00; C12N 5/02; C12N 1/00; C12N 15/00

[52] U.S. Cl. .................... 435/240.49; 435/172.1; 435/240.54; 435/320

[58] Field of Search .................... 47/58; 435/240, 241, 435/317, 172.2, 172.1

[56] References Cited

U.S. PATENT DOCUMENTS

| | | | |
|---|---|---|---|
| 3,816,960 | 6/1974 | Gudin et al. | 47/58 |
| 4,003,156 | 6/1975 | Sibi et al. | 47/58 |
| 4,038,778 | 8/1977 | Kadkade | 47/58 |
| 4,052,817 | 10/1977 | Seibert | 47/58 |

OTHER PUBLICATIONS

Chaleff et al., 1981, Md. Gen. Genet., 181:254–258.
Chaleff et al., 1978, Proc. Natl. Acad. Sci., U.S.A., 75(10):5104–5107.
Behki et al., 1976, "In Vitro Plant Regeneration from Leaf Explants of *Lycopersicon esculentum*", Can. J. Bot., vol. 54, pp. 2409–2414.
Evans et al., 1983, "Single Gene Mutations in Tomato Plants Regenerated from Tissue Culture", Science, vol. 221, pp. 949–951.
*The American Heritage Dictionary*, 1982, "Mutation", p. 825.
Murashige, 1979, "Plant Tissue Culture & Its Importance to Agriculture", in *Practical Tissue Culture Applications*, Academic Press, pp. 27–44.
Conger, (Editor), 1981, "*Cloning Agricultural Plants via In Vitro Techniques*", CRC Press, Inc. Boca Raton.
Paterson et al., "Detection of Altered Inhibition of Photosystem II Reactions in Herbicide-Resistant Plants", in Edelman et al., (Editors), *Methods in Chloroplast Molecular Biology*, Elsevier Biomedical Press, N.Y., 1982, pp. 109–118.
Chaleff, R. S., "Isolation of Agronomically Useful Mutants from Plant Cell Cultures", Science, vol. 219, pp. 676–682, (1983).
Orton, Tl J., "Experimental Approaches to the Study of Somoclonal Variation", *Plant Molecular Biology Reporter*, vol. 1, pp. 67–76, (1983).
Reisch, B., "Genetic Variability in Regenerated Plants", *Handbook of Plant Cell Culture*, D. A. Evans, et al., Editors, Chapter 25, pp. 748–769, (1983).
Sharpe, W. R. et al., "Plant Genetic Engineering: Designing Crops to Meet Food Industry Specifications", *Food Technology*, Feb. 1984, pp. 112–119.
Tran Thanh Van et al., "Plant Propagation: Nonidentical and Identical Copies", *Propagation of Higher Plants Through Tissue Culture*, pp. 134, 150–158, (1978).
D'Amato et al., "Nuclear Fragmentation Followed by Mitosis as Mechanism for Wide Chromosome Number Variation in Tissue Cultures: Its Implications for Plant Regeneration", Plant Cell Cultures: Results and Perspectives, pp. 67–72, (1980).
Meredith et al., "Genetic Variation in Cultured Plants", *Propagation of Higher Plants Through Tissue Culture*, pp. 166–176, (1978).
Locy, (1983), Can. J. Bot., 61: 1072–1079.
*Handbook of Plant Cell Culture:* vol. 1, 1, pp. 13–20, (Evans, Sharp, Ammirato & Yamada, Eds., 1983).
Zapata and Sink, 9, (1981), Theor. Appl. Genet., 59:265–268.
Chin et al., (1981), Plant Sci. Lett., 21:229–234.
Blair, (1982), Science '82: 77–76.
Larkin and Scowcroft, (1981), Theor. Appl. Genet., 60:197–214.
Evans et al., (1980), Physiol. Plant, 48:225–230.
Shephard et al., (1980), Science, 208:17–24.
Barbier et al., (1980), Ann. Amelior. Plantes, 30:321–344.
Ohki et al., (1978), Plant and Cell Physiol., 19:27–42.
Meredith, (1978), Plant Science Lett., 12:25–34.
Tal et al., (1977), Ann. Bot., 41: 937–941.
Vnuchkova, (1977), Soviet Plant Phys., 24 884–889.
Evans et al., (1976), Can. J. Genet. Cytol., 18: 57–65.
Kartha et al., (1976), Z. Pflanzenphysiol. Bd., 772.S.:292–301.
Padmanabhan et al., (1974), Can. J. Bot., 52:1429–32.

*Primary Examiner*—Thomas G. Wiseman
*Assistant Examiner*—David T. Fox
*Attorney, Agent, or Firm*—Banner, Birch, McKie and Beckett

[57] ABSTRACT

A method is provided of producing variant plant varieties of Lycopersicon spp. by tissue culture techniques employing 6-benzyladenine at high concentrations. The technique produces phenotypic variants that are the result of heritable nuclear genetic changes.

15 Claims, No Drawings

TISSUE CULTURES OF LYCOPERSICON SPP.

TECHNICAL FIELD

The present invention is directed to methods of tissue culturing plants of the genus Lycopersicon. More particularly, the present invention is directed to a method of developing genetically variant strains of plants from the genus Lycopersicon through tissue cultures.

BACKGROUND OF THE INVENTION

Historically, plant tissue culturing techniques have been employed primarily as a method of asexual propagation. These techniques allowed the rapid proliferation of plant lines. It was generally believed that all plants arising from a tissue culture would be genetically identical to the parental plant. While phenotypic variants were frequently observed among regenerated plants, their presence was considered undesirable to the goal of plant propagation and thus were generally ignored or discarded.

More recently, the potential of plant tissue culture techniques as a tool in the development of new plant varieties has been appreciated. See, e.g., Larkin and Scowcroft, (1981) *Theor. Appl. Genet.* 60: 197-214; Sibi et al., U.S. Pat. No. 4,003,156. Rather than ignore the variant plants developed from tissue cultures, it was observed that tissue culturing per se apparently led to phenotypic variants. While this variation associated with tissue culturing has been observed in a wide variety of species, the mechanism of the variations has not been elucidated.

The propagation of *Lycopersicon esculentum* by tissue culture is known. Padmanabhan et al., (1974) *Can. J. Bot.* 52: 1429-1432. There is no disclosure, however, of any phenotypic variants arising by the technique. It would be desirable, therefore, to develop a method of tissue culturing Lycopersicon spp. that results in a high number of phenotypic variants.

SUMMARY OF THE INVENTION

It is an object of the present invention to provide a method of producing variant strains of Lycopersicon spp.

It is another object of the present invention to provide a method of tissue culturing Lycopersicon spp.

It is also an object of the present invention to provide a method of tissue culturing Lycopersicon spp. that gives rise to a high number of variant strains.

A further object of the present invention is to provide a method of tissue culturing Lycopersicon spp. that produces phenotypic variants that are a result of heritable nuclear genetic changes.

These and other objects of the present invention are achieved by one or more of the embodiments below.

In one embodiment, the present invention provides a method of producing variant plant strains comprising: (a) regenerating a shoot from callus cells obtained from plant tissue on basal medium containing 6-benzyladenine (6-BA) at a concentration of at least about 5 uM, preferably at least about 10 uM, said plant being a member of the genus Lycopersicon; and; (b) rooting said regenerated shoot on a rooting medium or directly in soil.

In another embodiment, the present invention provides a method of producing variant plant strains comprising producing at least one rooted plantlet according to the above method, growing said rooted plantlet into mature plants and growing the seed from said mature plants.

DESCRIPTION OF THE PREFERRED EMBODIMENT

The present invention provides a method of developing variant plant varieties of Lycopersicon spp. in as little as two to four years. Traditional plant breeding techniques require as long as seven to eight years. Broadly, the present invention accomplishes this by employing 6-BA at unusually high concentrations in a basal medium. At these high concentrations of 6-BA, plants from calluses grown on basal media have shown significantly higher rates of phenotypic variation. The present invention, therefore, not only leads to more rapid development of new plant strains, but it also increases the probability of finding desirable strains since it increases the number of variations.

Applicants believe, but do not wish to be bound by the theory, that the 6-BA gives rise to variant strains by causing mutations in the genome of the plants. The theory is based, in part, on the following observations. While some plants exhibiting variant phenotypes also exhibit an increase or decrease in chromosome number, many variant phenotypes did not exhibit any change in chromosome number. Those plants exhibiting chromosomal variation were partially or completely sterile, while those variants exhibiting no change in chromosomal number could reproduce sexually and transmitted the new traits to their progeny. Furthermore, applicants have found that the number of variants produced is related to the concentration of 6-BA in the basal medium.

The process of the present invention involves several steps. First, tissue from a plant of the genus Lycopersicon is selected. A callus from the tissue is then grown on basal media containing 6-BA. Regenerated shoots from the callus are then rooted on a rooting media or potted directly in soil to obtain a plant. Usually, the seed from variant plants produced by the above method is gathered and then grown with controlled cross- and self-pollination. Desirable variants can then be selected and further propagated.

As is well known in the art, heritable nuclear genetic mutations segregate according to Mendelian ratios. That is to say that predictable ratios of progeny phenotypes occur when mutant plants are self-pollinated or cross-pollinated. For example, a heterozygous plant carrying a single recessive mutant allele when self-pollinated will yield progeny wherein the ratio of wild-type to their mutant siblings is about 3:1. If the heterozygous plant carries a single dominant mutation, self-pollination will yield progeny wherein the ratio of wild-type to their mutant siblings is about 1:3. If, on the other hand, the phenotypically variant plant is homozygous for the mutation, self-pollination will yield only variants as progeny. To determine the nuclear quality of such a mutation, back-crosses to wild-type plants may be performed. If the homozygous mutation is dominant and nuclear, only variant progeny should result regardless of which parent was the pollen donor. If the homozygous mutation is recessive, only phenotypically normal progeny will result, regardless of which parent was the pollen donor. If the mutation is non-nuclear, variant progeny will result only when the wild-type plant serves as pollen donor, but never when the mutant serves as pollen donor. These genetic tests, as well as others, are well known to those of skill in the art for determining the genetic basis of a phenotypic variation.

Callus formation has been reported from Lycopersicon spp. root tissue, arrested embryoids from cultured pollen cells, internodes and even stem, fruit and hypocotyl tissues from certain mutant strains. The preferred tissue, however, is leaf tissue. It is desirable to select young, fully expanded leaves.

The plant tissue is preferably sterilized prior to growing the callus. This prevents microorganisms, which grow faster than tissue, from contaminating the culture. Methods of sterilization are known in the art. A simple and economical method is to immerse the tissue in a 7% solution of household chlorine bleach (e.g., Clorox) for about 10 minutes and then rinse the tissue two or three times with sterile distilled water.

Sterile plant tissue is then transferred to a basal medium containing 6-BA. Basal media comprise inorganic nutrients, vitamins and a carbon source. The selection of an appropriate solid basal media is within the skill of the art. Several basal media are known, including but not limited to, B5 medium, White's medium and Schenk-Hildebrandt medium. See, e.g., Gamborg et al., (1976) *In Vitro* 12: 473-478. The preferred medium is that described by Murashage and Skoog, (1962) *Physiol. Plant.* 15: 473-497 (MS medium).

The present invention requires that 6-BA be present in the medium at a concentration of at least about 5 uM, preferably at least about 10 uM, to obtain the desired results. As noted above, the number of variant plants obtained is related to the concentration of the 6-BA. An increase in the number of variants has been observed as the 6-BA concentration was increased. It may be desirable, therefore, to increase the concentration of the 6-BA above 5 or 10 uM level. It has been found, however, that at concentrations above about 40 uM, the gain in variant plants is usually offset by a reduction in the total number of plants obtained. It is particularly preferred, therefore, to employ 6-BA in a concentration range of about 10 uM to about 40 uM.

It is also desirable to include another growth regulator, indole acetic acid (IAA), to aid the shoot formation in the callus. The preferred concentration range of IAA is from about 5 uM to about 10 uM. More or less IAA may be employed and such variations are readily within the skill of the art. Generally, however, IAA is employed at concentrations above 1 uM and below 20 uM.

Callus masses develop on the above media. Typically, shoots begin to appear in about three to four weeks. Calluses developed by the process of the present invention characteristically exhibit very few (e.g., 1-2) shoots per callus. The regenerated shoot can be transferred to a rooting medium or divided so that only a portion of the shoots is transferred to the rooting medium. The remaining callus is then recultured on fresh medium. Alternatively, the shoots can be rooted directly in soil.

The preferred rooting medium is that described for tobacco plants in Evans et al., (1980) *Physiol. Plant.* 48: 225-230. The disclosed medium is one-half strength MS medium containing 3-aminopyridine. Although not required, it is particularly preferred to add naphthylene acetic acid (NAA). Employing NAA increases the number of successfully rooted plants. The chance of losing a desirable variant because of the failure of a shoot to form roots, therefore, is reduced. The preferred concentration of 3-aminopyridine in the rooting media is about 74 uM and for the NAA is about 2 uM. Variations of the preferred rooting media are readily within the skill of the art.

Root formation will typically take 10 days when NAA is employed. Once roots are developed, the plantlets are transferred to pots and grown into mature plants. Seed can be collected from the various plants and then grown under controlled conditions in the field or a greenhouse. The selection and propagation of desirable variants from these plants are within the skill of the art.

The following example is included for illustrative purposes only and is not intended to limit the scope of the invention.

EXAMPLE

Seeds of a standard inbred processing tomato variety, UC82B (Stevens et al., 1978 Vegetable Crops Series #183, University of California 1978), were grown and plants with uniform normal morphology were identified as donor plants. Young, fully expanded tomato leaves were taken from the donor plants, sterilized by immersion in 7% Clorox for 10 minutes, and rinsed 2-3 times with sterile distilled water. Portions of the leaf tissue, approximately 5 cm×5 cm, were excised from the leaf with a sterile scalpel and asceptically transferred to a jar containing MS medium with the addition of 6-BA at a concentration of 10 uM and IAA at a concentration of 10 uM. A callus mass developed shortly and shoots were generated in three to four weeks.

Only one to two shoots were regenerated per explant. All regenerated shoots were transferred to a rooting medium comprised of one-half strength MS medium with 74 uM 3-aminopyridine and 2 uM NAA. Plantlets were recovered after about three to twelve weeks on the rooting medium. Between one and three plants were recovered from each explant that regenerated shoots.

Regenerated plants (R) were transferred to a greenhouse after being planted in soil. The R plants were self-fertilized and seed was collected from each regenerated plant to evaluate the next (R1) generation. Seed was collected from 230 R plants and grown in greenhouse flats for 60 days prior to transplanting in the field.

In addition to the well-characterized single gene mutations, other types of variants appeared. Variations in the number of chromosomes was frequently observed among R plants. All major chromosomal variants, however, were partially or completely sterile, so that by evaluating R1 plants, the recovery of single gene mutants was maximized. This procedure eliminated all variations without heritable basis (i.e., epigenetic variation), thus eliminating many of the undesirable variants recovered by Sibi et al., U.S. Pat. No. 4,003,156. In part, therefore, the present invention allows for the recovery of single gene nuclear mutations. See also the copending application entitled "Generation of Somaclonal Non-Mendelian Variants," U.S. Ser. No. 525,092, filed on even date herewith, the disclosure of which is expressly incorporated by reference herein.

R1 plants from each of the 230 R plants were evaluated in replicated plots in the field. A number of the R1 variants were identified that were either similar to previously reported mutants or could be clearly classified based on morphology. Thirteen possible genomic mutations were identified from the field plots of the 230 R1 plant-types. These mutant phenotypes are listed in Table 1 below. An examination of R1 segregation data suggests that most of the variants are simple Mendelian mutations. Each of the variants listed in Table 1 was regenerated from a separate leaf explant, and, therefore, represents a separate mutational event.

TABLE 1

Classification of mutated traits in the R1 Progeny of tomato plants regenerated in vitro grown in New Jersey.

| Mutant Character and Symbol | Regenerated Plant | Phenotype of R1 Normal | Phenotype of R1 Mutant | Genotype of Regenerated Plant |
|---|---|---|---|---|
| tangerine fruit (tv-tc1) | normal | 30 | 6 | +/tv |
| male sterile (ms-tc1) | normal | 29 | 10 | +/ms |
| male sterile (ms-tc2) | normal | 38 | 10 | +/ms |
| male sterile (ms-tc3) | normal | 36 | 6 | +/ms |
| male sterile (ms-tc4) | normal | 8 | 2 | +/ms |
| lethal albino (la-tc1) | normal | 64 | 19 | +/la |
| virescent (v-tc1) | normal | 42 | 4 | +/v |
| indeterminant (I-tc1) | indeterminant | 8 | 40 | I/+ |
| indeterminant (I-tc2) | indeterminant | 11 | 25 | I/+ |
| jointless pedicel (j-tc1) | normal | 9 | 2 | +/j |
| jointless pedicel (j-tc2) | jointless | 0 | 48 | j/j |
| green based fruit (G-tc1) | green base | 12 | 36 | G/+ |
| mottled leaf (m-tc1) | normal | 49 | 21 | +/m |

A detailed analysis of single plant selections of the next generation (R2) was completed in the greenhouse for eight of the twelve variants in Table 1. Two traits, ms-tc1 and G-tc1 were highly variable in the greenhouse in contrast to the field studies. These variants could not be adequately classified in the greenhouse. Field trials of ms-tc1, however, were completed. The remaining characteristics (tv-tc1, I-tc1, j-tc1 and j-tc2) were classified under field and greenhouse conditions. Homozygote and heterozygote genotypes of tv-tc1, I-tc1 and j-tc1 were identified from single plant selections. Seeds of the heterozygotes segregated in a 3:1 ratio. In addition, with the exception of G-tc1, each trait was observed in field trials in both New Jersey and California.

The above example is only one embodiment of the present invention. Other embodiments will readily occur to those skilled in the art. It is intended, therefore, that the present invention be limited only by the scope of the appended claims.

We claim:

1. A method of isolating heritable nuclear genetic variant plant strains comprising:
   (a) regenerating shoots from callus cells obtained from tissue of a plant on basal medium comprising 6-benzyladenine at a concentration of at least about 10 uM, said plant being from the genus Lycopersicon;
   (b) rooting said regenerated shoots on a rooting medium or directly in soil to provide plantlets;
   (c) growing said plantlets into mature plants and allowing the mature plants to self-fertilize;
   (d) collecting seed from said self-fertilized, mature plants;
   (e) growing said seed from self-fertilized plants to provide a second generation of plants;
   (f) selecting phenotypically variant plants from among said second generation of plants, said phenotypically variant plants bearing heritable nuclear genetic changes; and
   (g) confirming the nature of the heritable nuclear genetic changes by observing segregation ratios of phenotypically variant to wild-type siblings in said second generation, and when said segregation ratios do not conform to an approximately 3:1 or 1:3 ratio, performing backcrosses to wild-type plants and observing the progeny.

2. The method of claim 1 wherein said 6-benzyladenine is at a concentration ranging from about 10 uM to about 40 uM.

3. The method of claim 1 wherein said basal medium also comprises indole acetic acid.

4. The method of claim 1 wherein said basal medium also comprises indole acetic acid at a concentration ranging from about 5 uM to about 10 uM.

5. The method of claim 2 wherein said basal medium also comprises indole acetic acid.

6. The method of claim 2 wherein said basal medium also comprises indole acetic acid at a concentration ranging from about 5 uM to about 10 uM.

7. The method of claim 1 wherein said regenerated shoot is rooted on a rooting medium and said rooting medium comprises one-half strength Murashige and Skoog medium comprising 3-aminopyridine and naphthylene acetic acid.

8. The method of claim 2 wherein said regenerated shoot is rooted on a rooting medium and said rooting medium comprises one-half strength Murashige and Skoog medium comprising 3-aminopyridine and naphthylene acetic acid.

9. The method of claim 1 wherein said plant tissue is leaf tissue.

10. The method of claim 2 wherein said plant tissue is leaf tissue.

11. The method of claim 1 wherein the ratio of said phenotypically variant plants to their normal, wild-type siblings in said second generation is approximately 1:3.

12. The method of claim 1 wherein the ratio of said phenotypically variant plants to their normal, wild-type siblings in said second generation is approximately 3:1.

13. The method of claim 1 wherein said phenotypically variant plants have no normal, wild-type siblings in said second generation.

14. The method of claim 13 wherein said phenotypically variant plants, upon backcrossing with a wild-type, normal plant as pollen donor, yield no phenotypically variant progeny.

15. The method of claim 13 wherein said phenotypically variant plants, upon backcrossing with a wild-type, normal plant, using said variant plant as pollen donor, yield all phenotypically variant progeny.

* * * * *